United States Patent [19]

Ito

[11] Patent Number: 4,690,561
[45] Date of Patent: Sep. 1, 1987

[54] PARTICLE ANALYZING APPARATUS

[75] Inventor: Yuji Ito, Chigasaki, Japan

[73] Assignee: Canon Kabushiki Kaisha, Tokyo, Japan

[21] Appl. No.: 818,263

[22] Filed: Jan. 13, 1986

[30] Foreign Application Priority Data

| Jan. 18, 1985 | [JP] | Japan | 60-007038 |
| Jan. 18, 1985 | [JP] | Japan | 60-007039 |
| Jan. 18, 1985 | [JP] | Japan | 60-007040 |
| Jan. 19, 1985 | [JP] | Japan | 60-008101 |

[51] Int. Cl.$^4$ .................. G01N 21/00; G01B 11/00
[52] U.S. Cl. .................. 356/339; 356/73; 250/201
[58] Field of Search .......... 356/73, 336, 339; 250/201 AF

[56] References Cited

U.S. PATENT DOCUMENTS

| 4,363,962 | 12/1982 | Shida | 250/201 |
| 4,570,059 | 2/1986 | Iijima | 250/201 |
| 4,595,271 | 6/1986 | Suda et al. | 250/201 |
| 4,618,762 | 10/1986 | Hattori et al. | 250/201 |

Primary Examiner—R. A. Rosenberger
Attorney, Agent, or Firm—Fitzpatrick, Cella, Harper & Scinto

[57] ABSTRACT

There is disclosed a particle analyzing apparatus having an irradiating optical system for irradiating a particle to be examined, flowing in a flow section of a flow cell, with a light beam, a measuring optical system for measuring the light scattered by the particle, an optical detection system for projecting a positioning light beam onto a determined wall of the flow cell and detecting the light reflected from the wall, and a device for varying the relative position of the measuring optical system with respect to the flow cell according to the output of the optical detection system.

20 Claims, 15 Drawing Figures

PARTICLE ANALYZING APPARATUS

BACKGROUND OF THE INVENTION

1. Field of the Invention

The present invention relates to a particle analyzing apparatus, such as a flow cytometer, capable of positioning, i.e. focusing and/or alignment, of the measuring optical system with respect to the flow cell.

2. Description of the Prior Art

In a conventional particle analyzing apparatus employed for example in a flow cytometer, a particle to be examined, such as a blood cell, suspended in a sheath liquid and flowing through a flow section of a minute rectangular cross section of for example 200 $\mu m \times 200$ $\mu m$ at the center of a flow cell, is irradiated with light, and information on said particle, such as shape, dimention, refractive index, etc. can be obtained by measuring the forwarding or laterally scattered light. Also in a specimen which can be dyed with a fluorescent material, important information for particle analysis can be obtained by measuring the fluorescent light in a direction substantially perpendicular to the irradiating light.

For achieving a correct measurement for example in a flow cytometer, the light beam has to be correctly focused onto the particle to be examined or to the vicinity thereof by means of an objective lens, in order to avoid pseudo signals coming from other objects than the particle to be examined, and, for this purpose, the measuring optical system requires exact focusing. In the conventional apparatus, however, the focusing is conducted manually with a standard sample and with visual observation, prior to the actual measurement, and such focusing operation is not only cumbersome, but also inaccurate due to differences depending on examiners.

Also an eventual aberration in focusing, appearing in the course of measurement and caused for example by relative vibration of the flow cell with respect to the measuring optical system, cannot be detected. Consequently, since the absence of pseudo signals in the course of measurement cannot be detected, there remains certain ambiguity on the reliability of the obtained data.

In addition, the focusing operation has to be repeated whenever the flow cell or a nozzle for feeding the flow cell is replaced and an additional time is required for such focusing operation.

On the other hand, a very weak fluorescent signal has to be intensified for achieving fluorescent measurement, and, for this purpose, there have been proposed to employ a photomultiplier as the detector for the fluorescent light, to improve the light-emitting efficiency of the fluorescent material, to increase the power of irradiating light source, and to improve the light condensing power of the measuring objective lens. The improvement in the light-emitting efficiency of fluorescent material is the target of intensive developmental works. However, although the power of the irradiating light source can be considerably increased at the sacrifice of manufacturing cost, an excessively high power is not preferable because it may cause damage in the particle to be examined.

The condensing power of the objective lens can be improved by the use of a larger aperture, which however leads to a smaller focal depth. With such smaller focal depth, even a slight change in the distance between the flow section and the objective lens of the measuring optical system gives rise to introduction of noise signals from other objects, thereby prohibiting exact measurement. In this manner the conventional apparatus not only requires cumbersome focusing operation but also cannot provide a sufficient precision of analysis due to an insufficient intensity of the fluorescent signal.

In addition to the focusing of the measuring optical system to the flow cell explained above, the measuring optical system has to be aligned with the flow cell.

SUMMARY OF THE INVENTION

An object of the present invention is to provide a particle analyzing apparatus capable of easy and exact positioning of the measuring optical system with respect to the flow cell.

Another object of the present invention is to provide a particle analyzing apparatus capable of obtaining the fluorescent signal of a sufficiently high intensity, thereby improving the accuracy of measurement.

Still another object of the present invention is to provide a particle analyzing apparatus capable of simultaneously detecting the states of focusing and axial alignment of the measuring optical system with respect to the flow cell.

BRIEF DESCRIPTION OF THE DRAWINGS

FIGS. 5 to 7 illustrate an embodiment employing four elements, wherein

FIGS. 8 to 10 illustrate an embodiment employing the measuring objective lens in a positioning detecting system, wherein

FIGS. 11 to 13 illustrate an embodiment employing an external wall of the flow cell as a reference for positioning, wherein

DESCRIPTION OF THE PREFERRED EMBODIMENTS

Figure 1:
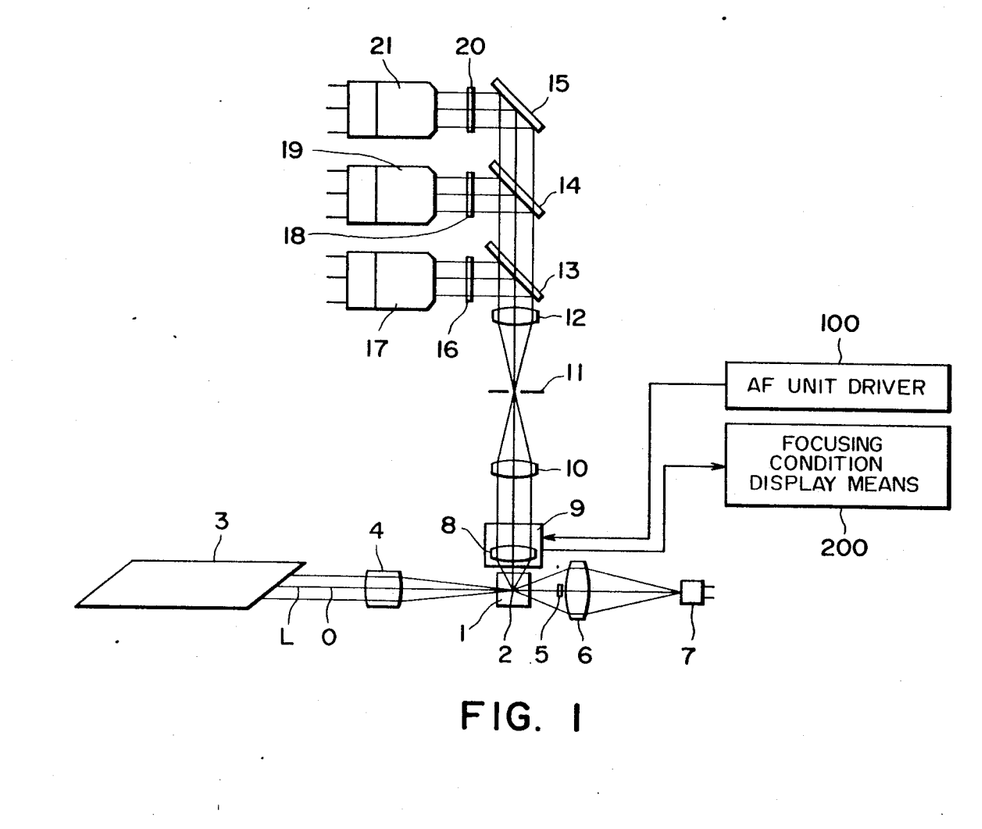
FIG. 1 is a schematic view showing the structure of a first embodiment of the present invention.

Referring to FIG. 1, a particle S to be examined passes through a flow section 2, particularly through a central portion thereof, extended in a direction perpendicularly to the plane of drawing at the center of a flow cell 1, and a laser unit 3 is provided in a direction perpendicular to the flow of said particle. On an optical axis O of a laser beam L emitted by said laser unit 3, there is provided, between said particle S and the laser unit 3, an imaging lens 4 composed of two cylindrical lenses to each other orthogonal. Also on said optical axis O, opposite to the laser unit 3 with respect to the particle S, there are provided a light shield plate 5, a condenser lens 6 and a photoelectric detector 7 in this order.

Also in a direction substantially perpendicular to the optical axis O of the laser beam L and also to the flowing direction of the particle S, there are provided in succession an auto-focusing (AF) unit 9 containing a measuring objective lens 8; a condenser lens 10, a diaphragm plate 11, a condenser lens 12; and wavelength selecting means 13, 14, 15 composed for example of dichroic mirrors, and, on optical paths of light beams reflected by said wavelength selecting means 13, 14, 15, there are respectively provided barrier filters 16, 18, 20 and photoelectric detectors 17, 19, 21, composed for example of photomultipliers capable of detecting very weak light by amplification.

Thus the laser beam L emitted by the laser unit 3 is formed as a beam having any expectative major and minor axes by the lens 4 composed of mutually orthogonal two cylindrical lenses, and irradiates the particle S flowing in the flow section 2. The light scattered by the particle S in the forward direction is received by the photo-electric detector 7 through the condenser lens 6, after elimination of non-scattered light by the shield plate 5, for measuring the properties of said particle S.

For a particle S dyed with various fluorescent materials, light scattered in the lateral direction is guided through the measuring objective lens 8 in the autofocusing unit 9 and focused by the condenser lens 10 onto the diaphragm plate 11. Noise level can be reduced in the obtained signal by having the laterally scattered light and the fluorescent light passed through said diaphragm plate 11 which is optically conjugate with the particle S to be examined. After passing through said diaphragm plate 11, the light beam is converted into a parallel beam by the condenser lens 12, and is divided, by the wavelength selecting means of a suitable spectral characteristic, into the laterally scattered light and the fluorescent light. The laterally scattered light is detected by the barrier filter 16 and the photoelectric detector 17 for observing the granularity inside the particle S. On the other hand, the fluorescent light, after passing through the wavelength selecting means 13, is divided for example into green fluorescent light and red fluorescent light by means of the wavelength selecting means 14, and said green fluorescent light is detected by the barrier filter 18 and the photoelectric detector 19 while said red fluorescent light is guided through the wavelength selecting means 15 and the barrier filter 20 and detected by the photoelectric detector 21, for observing biochemical properties of the particle.

The wavelength selecting means 14 or 15 for selecting fluorescent light is composed of a dichroic mirror for example of green and red, but there can also be employed a spectral prism or a diffraction grating capable of continuous separation of wavelength. Also beam diameter varying means such as a beam expander or a beam compressor may be inserted between the light source 3 and the lens 4.

Figure 2:
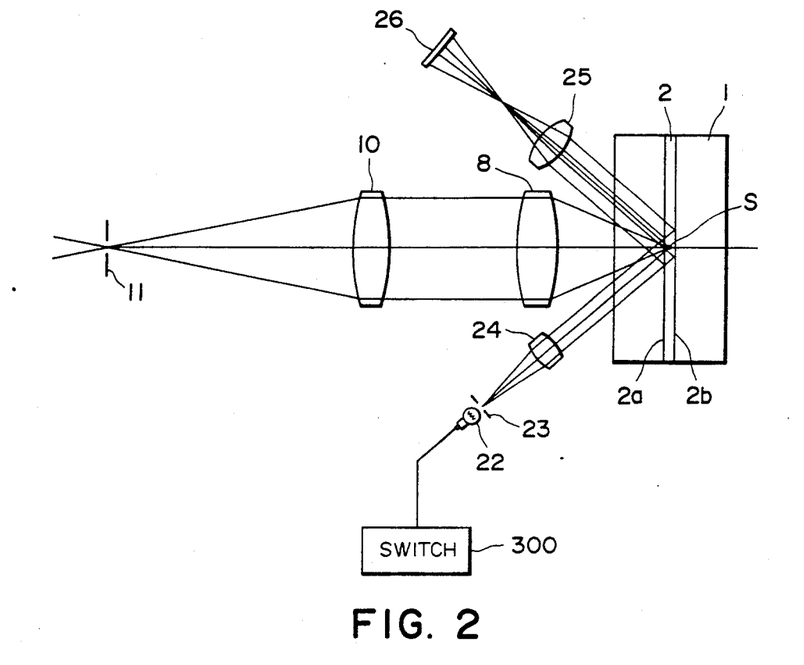
FIG. 2 is a lateral view of an optical system of an auto-focusing unit.
Figure 3:
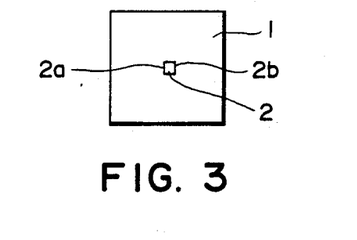
FIG. 3 is a cross-sectional view of a flow cell.
Figure 4:
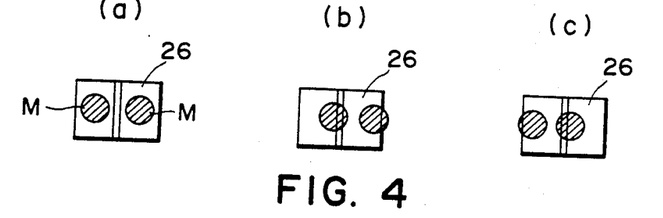
FIGS. 4(a), 4(b) and 4(c) are schematic views showing various distribution of light images on divided elements.

In the following, there will be given an explanation on the auto-focusing unit 9 capable of improving the efficiency of collecting weak light and still capable of accurate focusing, while making reference to FIGS. 2 to 4, wherein FIG. 2 is a lateral view of the auto-focusing unit 9 and FIG. 3 is a horizontal cross-sectional view of the flow cell 1. The measuring objective lens 8 is located at the center of said auto-focusing unit 9, and a light source 22 is provided thereunder to irradiate the flow cell with a light beam. On the optical axis of said light source 22 there are provided, in succession, an aperture 23, and a convex lens 24 having a focal point on said aperture 23 to obtain a parallel positioning beam. Also a convex lens 25 and divided elements 26 are provided on a path of light reflected by a front internal wall 2a and a rear internal wall 2b of the flow section 2.

The objective lens 8 is so positioned as to convert the light beam from the flow section 2 into a parallel beam when said objective lens 8 is focused to the center of the flow section 2, and the focusing optical system in the auto-focusing unit 9 is so positioned as to detect said front wall 2a and rear wall 2b in said state. More specifically, the light beam from the light source 22 is guided through the aperture 23 and the convex lens 23, and is projected onto the front wall 2a and the rear wall 2b. Two images of said aperture reflected respectively by said walls are focused on the divided elements 26 through the convex lens 25.

The divided element 26 has two sections and is so positioned that, when the objective lens 8 is in focus, two images of the aperture 23 are formed in equal sizes respectively on two sections of the divided element 26, as shown in FIG. 4(a), thereby releasing mutually equal output signals from said two sections. An out-of-focus state of the objective lens 8 can be identified if the images M of the aperture are displaced laterally to generate mutually different signals from two sections, as shown in FIGS. 4(b) and 4(c).

Thus, when two sections of the divided element 26 generate mutually equal output signals, the objective lens 8 is correctly focused to the center of the flow section 2, wherein the objective lens 8 provides a parallel light beam representing the particle to be examined. As the diaphragm plate 11 is disposed at the converging point by the condenser lens 10, the flow section becomes optically conjugate with the diaphragm plate 11 when the focusing is achieved by the movement of the auto-focusing unit 9, whereby the scattered light from the particle S is correctly converged to the diaphragm plate 11.

Since the objective lens 8 and the condenser lens 10 are so combined as to have a parallel beam, the focusing can be achieved by so moving the autofocusing unit 9 as to obtain two equal output signals from the divided element 26, even if the flow cell 1 is axially displaced at the replacement thereof. Also since the focusing relies on the reflection in the flow section, the focusing operation is not affected even if the size of the flow cell, or the distance from the surface thereof to the flow section 2 is somewhat varied.

As explained in the foregoing, in the present embodiment, easy and accurate focusing can be achieved by integrally moving the auto-focusing unit 9, including the objective lens 8, light source 22, aperture 23, convex lenses 24, 25 and divided element 26, in the axial direction of the objective lens 8 with respect to the flow cell, by means of a unit driving mechanism 100 and according to the output signals of the divided element 26. It is therefore rendered possible to increase the aperture of the objective lens 8 and to improve the light-collecting efficiency of the optical system to elevate the signal intensity while maintaining an exact in-focus state. The wavelength of the focusing light source 22 is preferably different from that of the laser unit 3 or of the fluorescent light, in order to avoid eventual influence on the measurement, for example by scattering in the flow cell 1, and is conveniently selected in the infrared range.

Automatic focusing can be achieved by driving the unit driving mechanism 100 with the output signals of the divided element 26 along the optical axis until two images M of the aperture 23 are respectively focused on two sections of said element 26, and a further improvement in operability can be attained in this manner. Also an inaccurate measurement, when the objective lens 8 is not focused, can be avoided by initiating the measurement in the particle analyzing apparatus with a signal indicating that the driving mechanism for the auto-focusing unit 9 is stopped or with an output signal from the divided element 26 indicating an in-focus state. Also there may be provided means 200 indicating that the image M of the aperture 23 is focused on a pre-determined position of the divided element 26, and in case of manual operation of the auto-focusing unit 9, the measurement can be initiated when said signal is indicated.

Furthermore, instead of moving the autofocusing unit 9, it is also possible to move the flow cell 1.

Also the arrangement of the focusing optical system in the auto-focusing unit 9 is not limited to that shown in the foregoing embodiment. For example, the light source 22 may be positioned above the measuring objective lens 8. Also in the foregoing embodiment the auto-focusing unit 9 is placed in the measuring optical system for the laterally scattered light, but a similar effect can be obtained by placing an auto-focusing unit between the shield plate 5 and the condenser lens 6 in the measuring opticla system for the forward scattered light. Naturally a further improved result can be obtained by placing such auto-focusing units both in the measuring optical systems for the laterally and forward scattered lights.

A switch 300 shown in FIG. 2 is opened or closed respectively when the positioning light beam is measured or not. The positioning state may be displayed after the measurement of the light beam.

Figure 5:
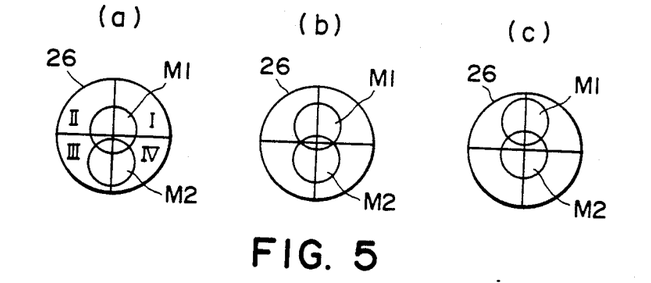
FIGS. 5(a), 5(b) and 5(c) are schematic views showing distribution of light images on said elements in detecting the state of focusing.
Figure 6:
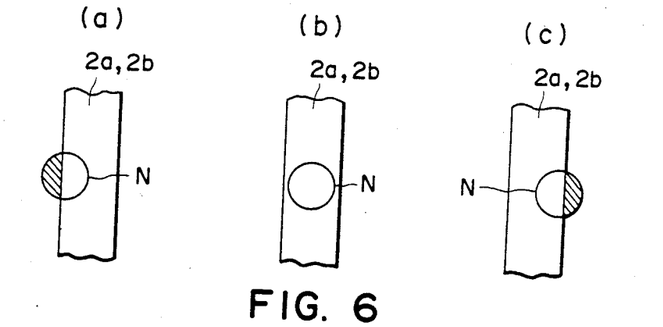
FIGS. 6(a), 6(b) and 6(c) are schematic views showing the irradiating beam in the flow section at detection of focusing state.
Figure 7:
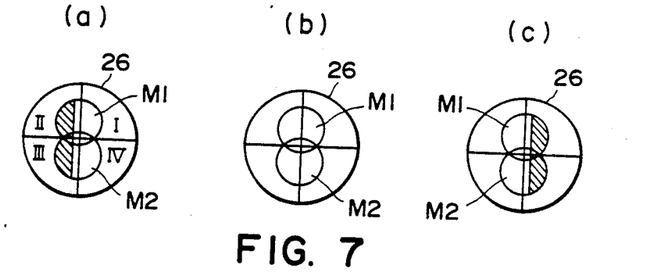
FIGS. 7(a), 7(b) and 7(c) are schematic views showing the distribution of light images on the divided elements at detection of focusing state and alignment.

In the following there will be explained another embodiment, as shown in FIGS. 5 through 7, in which the element 26 is divided into four sections. When the objective lens 8 is in focus as shown in FIG. 2, images M1, M2 of the aperture 23 respectivley reflected by two internal walls of the flow section are formed in equal sizes respectively on sections I and II, and the other sections III and IV of the divided element 26, as shown in FIG. 5(b). The element 26 is so positioned as to provide a relation: P1+P2=P3+P4 in the in-focus state, wherein P1, P2, P3 and P4 are respective outputs of the sections I, II, III and IV of said element 26. Thus, if P1+P2≠P3+P4 as shown in FIG. 5(a) or 5(c), the objective lens 8 is not properly focused.

Consequently, if the outputs of the element 26 satisfies the relation P1+P2=P3+P4, the objective lens 8 is always focused to the center of the flow section 2 and provides a parallel beam representing the image of the particle S to be examined. As the diaphragm plate 11 is provided at the converging point by the condenser lens 10, the flow section 2 becomes optically conjugate with said diaphragm plate 11 when the focusing is achieved by axial movement of the auto-focusing unit 9, so that the light scattered by the particle S is accurately collected to the position of the diaphragm plate 11.

In addition to the focusing function explained above, the use of 4-sectioned element 26 enables simultaneous alignment of the optical axis. By placing the auto-focusing unit 9 in such a manner that the irradiating light beam N falls on the flow section 2 as shown in FIG. 6(b) when the center of the flow section 2 is aligned with the optical axis, a misalignment can be identified by displacement of the light beam N from the flow section 2 as shown in FIG. 6(a) or 6(c).

The states as shown in FIGS. 6(a) to 6(c) respectively correspond to the light image distributions on the element 26 as shown in FIGS. 7(a) to 7(c). The outputs of the element 26 satisfy a relation: P1+P4=P2+P3 in case of proper alignment, or P1+P4≠P2+P3 in case of misalignment. FIG. 7(b) shows the distribution of the images M1, M2 of the aperture on the divided element 26 in case proper focusing and proper alignment are simultaneously achieved. In this case the outputs of the element 26 satisfy relations P1+P2=P3+P4 and P1+P4=P2+P3, so that P1=P2=P3=P4.

FIGS. 7(a) and 7(c) show cases in which focusing is properly achieved but not the alignment, as shown in FIG. 5(a) or 5(c). In such case the outputs the element 26 provide a result P2+P3<P1+P4 or P1+P4<P2+P3, since light is not reflected from a portion of the beam overflowing the flow section 2. Consequently the condition P1=P2=P3=P4 for proper focusing and alignment does not stand in this case. In this manner it is rendered possible to simultaneously identify the state of focusing and alignment by comparing the outputs of the element 26 and identifying whether said outputs are mutually equal.

Since the objective lens 8 and the condenser lens 10 are so combined as to have a parallel light beam therebetween, the focusing and alignment can be achieved by forming the images M1, M2 of the aperture 23 respectively on proper positions on the divided element 26 through displacement of the auto-focusing unit 9 by means of a unit driving mechanism 100, even if the central position of the flow cell 1 is somewhat displaced axially or otherwise at the replacement of the flow cell 1.

Figure 8:
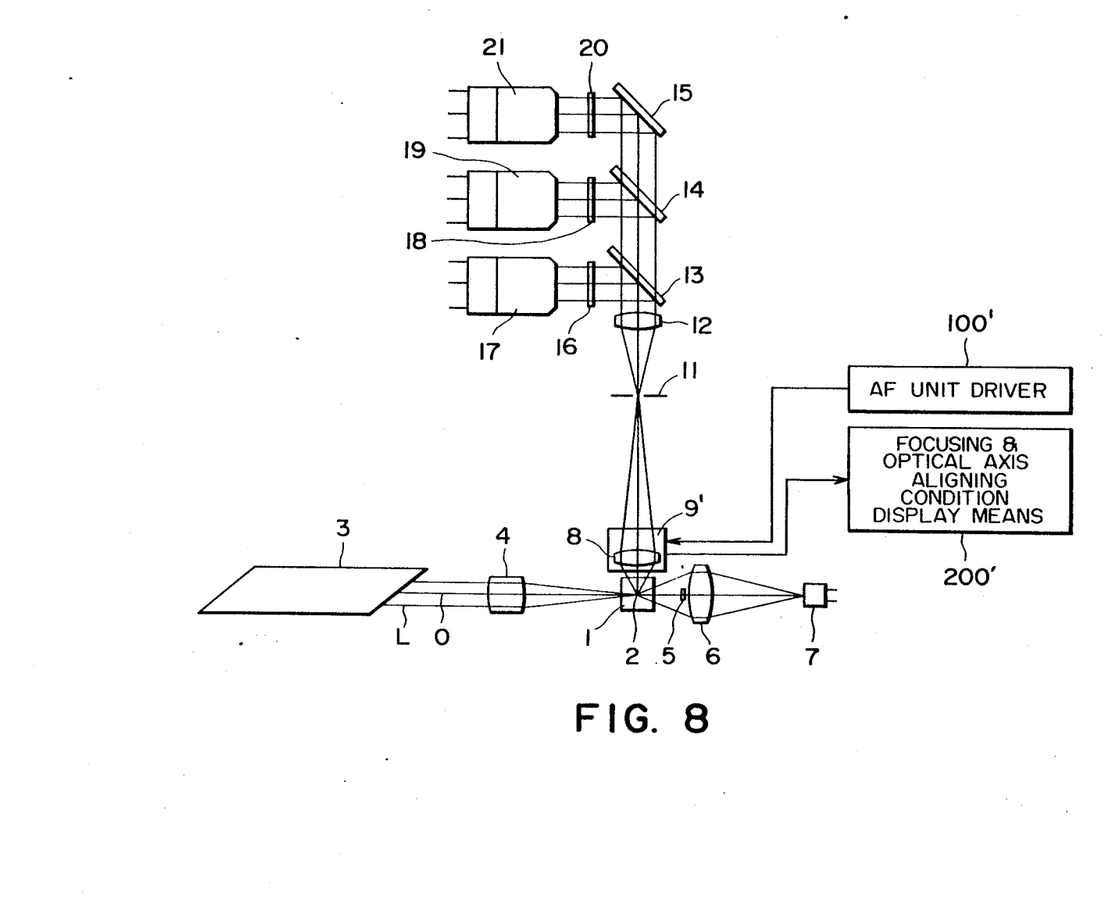
FIG. 8 is a schematic view of an optical system.
Figure 9A:
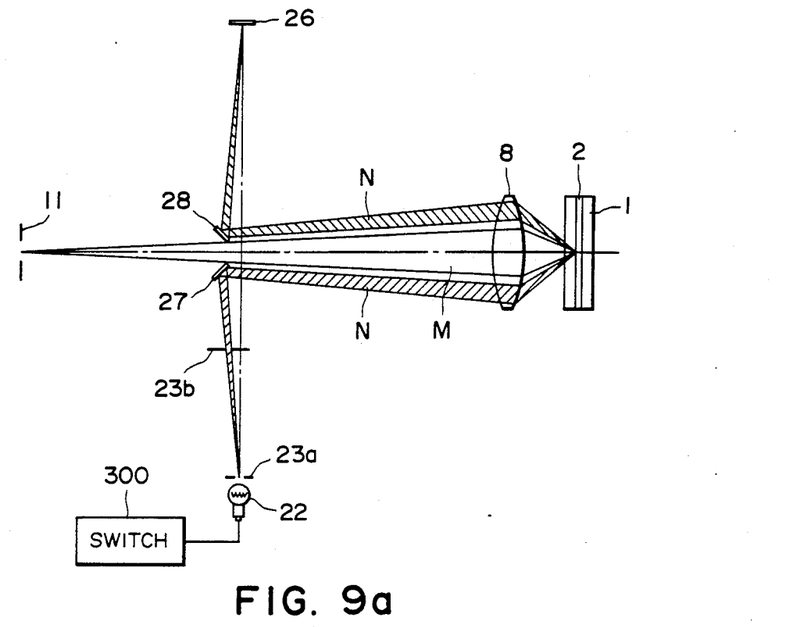
FIG. 9(a) is a lateral view of an optical system of an auto-focus auto-alignment unit.
Figure 9B:
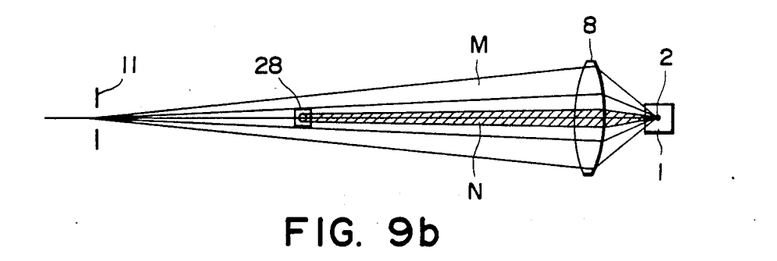
FIG. 9(b) is a plan view of said optical system.
Figure 9C:
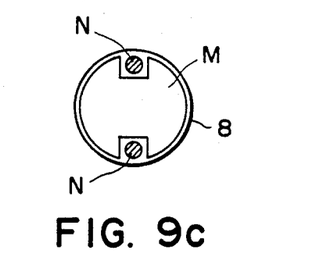
FIG. 9(c) is a schematic view showing the relationship between the measuring light beam and the focus-alignment detecting beam.
Figure 10:
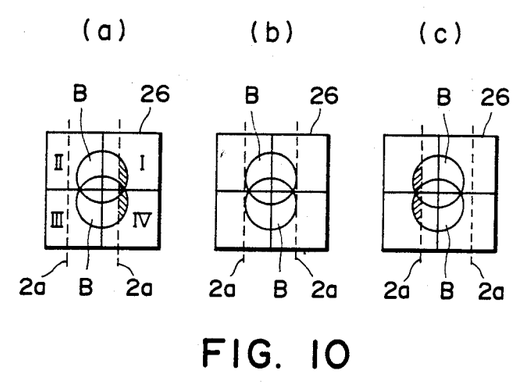
FIGS. 10(a) to 10(c) are schematic views showing the distribution of light images on the four elements.

In the following there will be explained another embodiment, as shown in FIGS. 8-10 in which the measuring objective lens is also utilized for focusing and alignment. In FIG. 8, the same components as those in FIG. 1 are represented by the same numbers, except that AF driver unit 100, focusing condition display means 100, and auto-focusing unit 9 are, respectively, AF driver unit 100', focusing and optical axis aligning condition display means 100', and auto-focusing and alignment unit 9'; FIG. 9(a) is a schematic lateral view of an auto-focusing alignment unit 9, and FIG. 9(b) is a plan view thereof. In said auto-focusing unit 9', a measuring objective lens 8 is provided in a position closer to the flow cell, and a focus/axis detecting light source 22 is provided at the lower left portion to emit a light beam in a direction substantially perpendicular to the optical axis of the objective lens 8. Apertures 23a, 23b are provided in succession on the light path of said light source 22, and a mirror 27 is provided in the light path of the light source 22 and in the vicinity of the optical axis of said objective lens 8. Furthermore, a mirror 28 is provided in the upper left portion of the unit 9' and in the vicinity of the optical axis of the objective lens 8, and a 4-sectioned element 26 is provided at a position substantially symmetrical with the aperture 23a with respect to the optical axis of the objective lens 8. The aperture 23a and the 4-sectioned element 26 are both located, like the aperture 11, at the focal point of the objective lens 8. The mirrors 27, 28 are so adjusted that the light beam N from the light source 22 and the incident light beam to the 4-sectioned element 26 pass above and below the measuring light beam M through the objective lens 8 when seen in lateral view as shown in FIG. 9(a), but pass the center of said light beam M when seen in plan view as shown in FIG. 9(b). Thus, in a cross-sectional view crossing the optical axis of the objective lens 8, as shown in FIG. 9(c), the measuring light beam M partially overlaps, at top and bottom, with said focusing-aligning light beams N, but such overlapping scarcely affects the precision of measurement.

The light beam from the light source 22 passing through the aperture 23a is further limited by the aperture 23b to a size suitable for entering the mirror 27, then deflected by said mirror 27 toward the objective lens 8, again deflected by the lower part of the objective lens 8 and reflected by the front wall and rear wall of the flow section 2 of the flow cell 1. The reflected light beam N is deflected again by the objective lens 8, then reflected by the mirror 28 and forms two images B of the aperture 23a on the 4-sectioned element 26.

FIG. 10 shows the relationship between two images B of the aperture 22 on the element 26 with four sections I, II, III and IV and the width 2a of the flow section 2. The element 26 is so adjusted that, when the objective lens 8 is in focus, two images B of the aperture 23a reflected respectively by the front and rear walls of the flow section 2 are formed in a same size respectively in the sections I, II and in the sections III, IV. Thus the state of focusing can be identified by identifying whether P1+P2 is equal to P3+P4, wherein P1, P2, P3 and P4 are respective outputs of the sections I, II, III and IV.

In case of misalignment, the focusing-aligning light beam N is displaced from the center of the flow section, partially overflowing the width 2a of the flow section 2, and such over-flowing beam does not generate reflection. Thus, in FIG. 10(a) the amount of the light is reduced in the hatched areas in the sections I and IV, while in FIG. 10 (c) the amount of light is reduced in the hatched areas in the sections II and III. Consequently the state of alignment can be identified by a comparison of P1+P4 and P2+P3. FIG. 10 (b) shows the positions of the images B on the 4-sectioned element 26 in case of focused and aligned state, satisfying the condition for focusing P1+P2=P3+P4 and the condition for alignment P1+P4=P2+P3, which lead to the condition for focusing and alignment P1=P2=P3=P4. In this manner it is rendered possible to identify the state of focusing and alignment by comparing the output signals of the 4-sectioned element 26.

Also in case that these output signals are not all equal, it is still possible to compare P1+P2 with P3+P4 and compare P1+P4 with P2+P3 to identify whether the lens is focused too far or too close and whether the optical axis is misaligned to left or right, thus enabling immediate correction of the apparatus.

As explained above, the foregoing embodiment enables easy and accurate focusing. It is therefore rendered possible to increase the aperture of the measuring objective lens 8, thereby improving the converging efficiency of the optical system and elevating the intensity of the measured signal, while maintaining accurate focusing.

The wavelength of the focusing-aligning light source 22 is preferably separated from that of the laser unit 3 or of the fluorescent light, and is conveniently selected in the infrared range.

Figure 11:
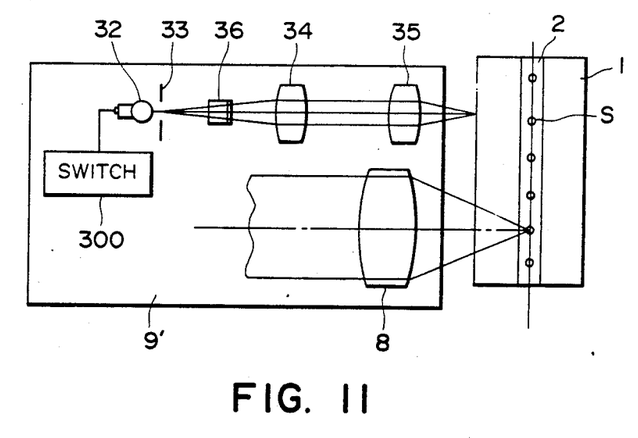
FIG. 11 is a lateral view of an optical system of an auto-focusing unit.
Figure 12:
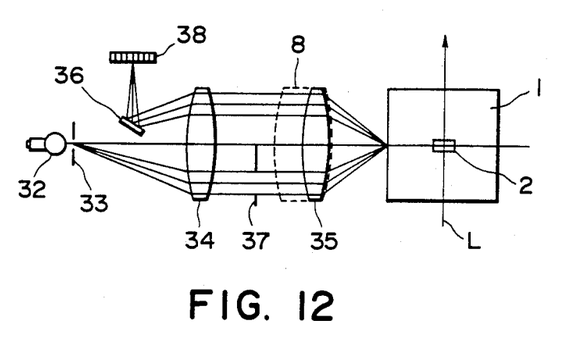
FIG. 12 is a plan view of said optical system.
Figure 13:
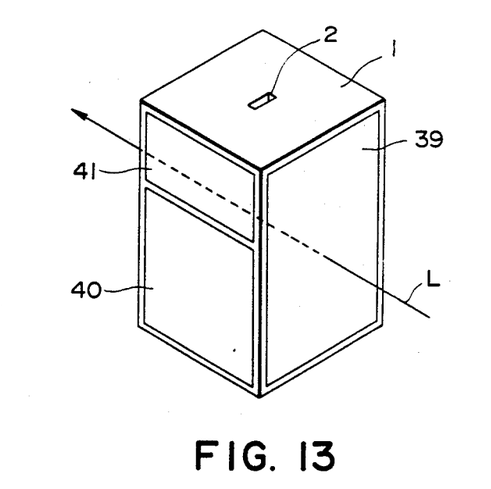
FIG. 13 is a perspective view of a flow cell provided with various coatings.

In the foregoing embodiments the positioning, including focusing and alignment, is achieved, taking the internal walls of the flow section in the flow cell as references. In the following there will be explained another embodiment, as shown in FIGS. 11 through 13 and, in which the focusing is achieved, using the external walls of the flow cell as references. The particle analyzing system is the same as that shown in FIG. 1.

FIG. 11 is a lateral view of an auto-focusing unit 9', and FIG. 12 is a plan view thereof. An objective lens 8 is provided in the lower part of said unit 9', and a light source 32 is provided in the upper part to irradiate a flow cell 1 with light. On the optical axis of said light source 32 there are provided, in succession, an aperture 33, and convex lenses 34, 35. A mirror 36 is provided between the aperture 33 and the convex lens 34 and lateral to the optical axis, and a diaphragm plate 37 is provided between the convex lenses 34, 35 and at the opposite side with respect to said optical axis. Furthermore a position detector 38 is provided at a position for receiving a light beam reflected by the mirror 36.

The objective lens 8 is so positioned as to convert the light beam from the flow section 2 into a parallel beam when said objective lens 8 is focused to the center of the flow section 2, and the optical system in the upper part of the auto-focusing unit 9' is adjusted to detect the external surface of the flow cell in this state. More specifically, the light from the light source 32 is guided through the convex lens 34, diaphragm 37 and convex lens 35 to project the image of the aperture 33 onto the external surface of the flow cell 1, and the slit image of the aperture 33, reflected by said external surface, is focused on the position detector 38 through the convex lenses 34, 35 and mirror 36. In the state illustrated in FIGS. 11 and 12, wherein the objective lens 8 is focused, the bit position of the slit image of the aperture 33 on the position detector 38 indicates such focused state.

As explained above, if the distance from the center of the flow section 2 to the external surface of the flow cell 1 is known, the objective lens 8 is always focused to the center of the flow section 2 when the aperture 33 is focused onto the external surface of the flow cell 1 through the convex lenses 34, 35 whereby the objective lens 8 provides a parallel beam representing the image of the particle S. Since the diaphragm plate 11 is located at the converging position by the condenser lens 10 as shown in FIG. 1, the flow section 2 becomes optically conjugate with the diaphragm plate 11 when the focusing is achieved by the movement of the autofocusing unit 9', so that the light scattered by the particle S is precisely concentrated to the position of the diaphragm plate 11.

FIG. 13 is a perspective view of the flow cell 1 so improved as to be used in combination with the above-explained auto-focusing unit 9'. A face 39 receiving the laser beam L is provided with a transmission coating adapted to the wavelength of the laser beam L, while a measuring face 40, provided in the lower part of a face orthogonal to the above-mentioned face 39, is provided with a transmission coating efficiently transmitting the wavelength range for measurement, and a focusing face 41, located above said measuring face 40 is provided with a reflective coating efficiently reflecting the light of a wavelength range emitted from the focusing light source 32.

The wavelength of the focusing light source is preferably different from that of the laser unit 3 shown in FIG. 1 or of the fluorescent light, and is conveniently selected in the infrared wavelength range. Consequently a coating efficiently reflecting infrared light can be selected as the reflective coating on the focusing face 41. The use of such flow cell allows to obtain sharp images of the aperture 33 on the position detector 38.

We claim:

1. A particle analyzing apparatus comprising:
    an irradiating optical system for irradiating a particle to be examined with a light beam, wherein said particle flows in a flow section in a flow cell comprising said flow section wherein said flow cell has two opposed inner walls;
    a measuring optical system for measuring light scattered by said particle;
    an optical detection system for projecting a positioning light beam onto said flow cell and detecting the light reflected by said two opposed internal walls; and
    means for varying the relative position of said measuring optical system with respect to said flow cell in response to the output of said optical detection system.

2. A particle analyzing apparatus according to claim 1, wherein the positioning light beam projected onto said flow cell is a parallel beam.

3. A particle analyzing apparatus according to claim 1, wherein said optical detection system is provided with a photodetector element divided into two sections.

4. A particle analyzing apparatus according to claim 1, wherein said optical detection system is provided with a photodetector element divided into four sections.

5. A particle analyzing apparatus according to claim 1, wherein said optical detection system is provided with a position detector element.

6. A particle analyzing apparatus according to claim 1, wherein said optical detection system is provided with a detecting lens which is different from an objective lens of said measuring optical system.

7. A particle analyzing apparatus according to claim 1, wherein said optical detection system utilizes, as a detection lens, an objective lens of said measuring optical system.

8. A particle analyzing apparatus according to claim 1, wherein said optical detection system is incorporated in a same unit, together with the objective lens of said measuring optical system.

9. A particle analyzing apparatus according to claim 8, wherein said unit is rendered movable in the direction of optical axis of said measuring optical system and/or in a perpendicular direction thereto.

10. A particle analyzing apparatus according to claim 1, whereby said optical detection system utilizes light of a wavelength range which is outside of the wavelength range utilized in the measurement of said measuring optical system.

11. A particle analyzing apparatus according to claim 12, wherein said optical detection system utilizes light in the infrared range.

12. A particle analyzing apparatus according to claim 1, wherein relative positioning of said measuring optical system with respect to said flow cell is automatically conducted.

13. A particle analyzing apparatus according to claim 1, wherein said measuring optical system is provided with a diaphragm aperture which is optically conjugate with the particle to be examined.

14. A particle analyzing apparatus according to claim 1, further comprising display means for displaying the state of focusing and/or alignment according to the output of said optical detection system.

15. A particle analyzing apparatus according to claim 1, further comprising switch means which turns off the positioning light beam during light measurement and turns on said positioning light beam when light measurement is not conducted.

16. A particle analyzing apparatus according to claim 5, wherein the state of positioning is displayed after said light measurement.

17. A particle analyzing apparatus according to claim 1, wherein said means for varying the relative position of said measuring optical system with respect to said flow cell is movable along an optical axis of said measuring optical system.

18. A particle analyzing apparatus according to claim 1, wherein said means for varying the relative position of said measuring optical system with respect to said flow cell is movable in a plane perpendicular to an optical axis of said measuring optical system.

19. A particle analyzing apparatus according to claim 1, wherein said means for varying the relative position of said measuring optical system with respect to said flow cell is movable along an optical axis of said measuring optical system and in a plane perpendicular to said optical axis.

20. A particle analyzing apparatus according to claim 1, wherein said flow section comprises said two opposed inner walls.

* * * * *

UNITED STATES PATENT AND TRADEMARK OFFICE
CERTIFICATE OF CORRECTION

PATENT NO. : 4,690,561
DATED : September 1, 1987
INVENTOR(S) : YUJI ITO

It is certified that error appears in the above-identified patent and that said Letters Patent is hereby corrected as shown below:

COLUMN 4

Line 24,   "23," should read --24,--.

COLUMN 6

Line 51,   "display means 100," should read --display means 200,--.
    Line 54,   "display means 100'," should read --display means 200',--.
    Line 55,   "unit 9';" should read --unit 9'.--.
    Line 56,   "focusing alignment unit 9," should read --focusing and alignment unit 9',--.

COLUMN 10

Line 8,    "whereby" should read --wherein--.
    Line 33,   "5," should read --15,--.

Signed and Sealed this

Ninth Day of February, 1988

Attest:

DONALD J. QUIGG

Attesting Officer      Commissioner of Patents and Trademarks